United States Patent [19]

Hirschfeld

[11] 4,037,760

[45] July 26, 1977

[54] PROPORTIONAL DILUTER

[75] Inventor: Tomas Hirschfeld, Framingham, Mass.

[73] Assignee: Block Engineering, Inc., Cambridge, Mass.

[21] Appl. No.: 679,564

[22] Filed: Apr. 23, 1976

[51] Int. Cl.² .................... B67D 5/60; G01F 11/26
[52] U.S. Cl. ................................ 222/145; 23/292; 222/454
[58] Field of Search ............... 23/292; 222/454, 455, 222/164, 145

[56] References Cited

U.S. PATENT DOCUMENTS 2,324,580  7/1943  Hight ............................. 222/145
3,651,990  3/1972  Cornei ......................... 222/145 X Primary Examiner—Robert B. Reeves
Assistant Examiner—Hadd Lane
Attorney, Agent, or Firm—Schiller & Pandiscio

[57] ABSTRACT

A device for generating a multiplicity of proportionally diluted samples from a parent solution, which device has a plurality of chambers so connected that as the system is oscillated about a single axis, a proportional part of the fluid in each chamber is sampled and delivered to the next chamber.

14 Claims, 6 Drawing Figures

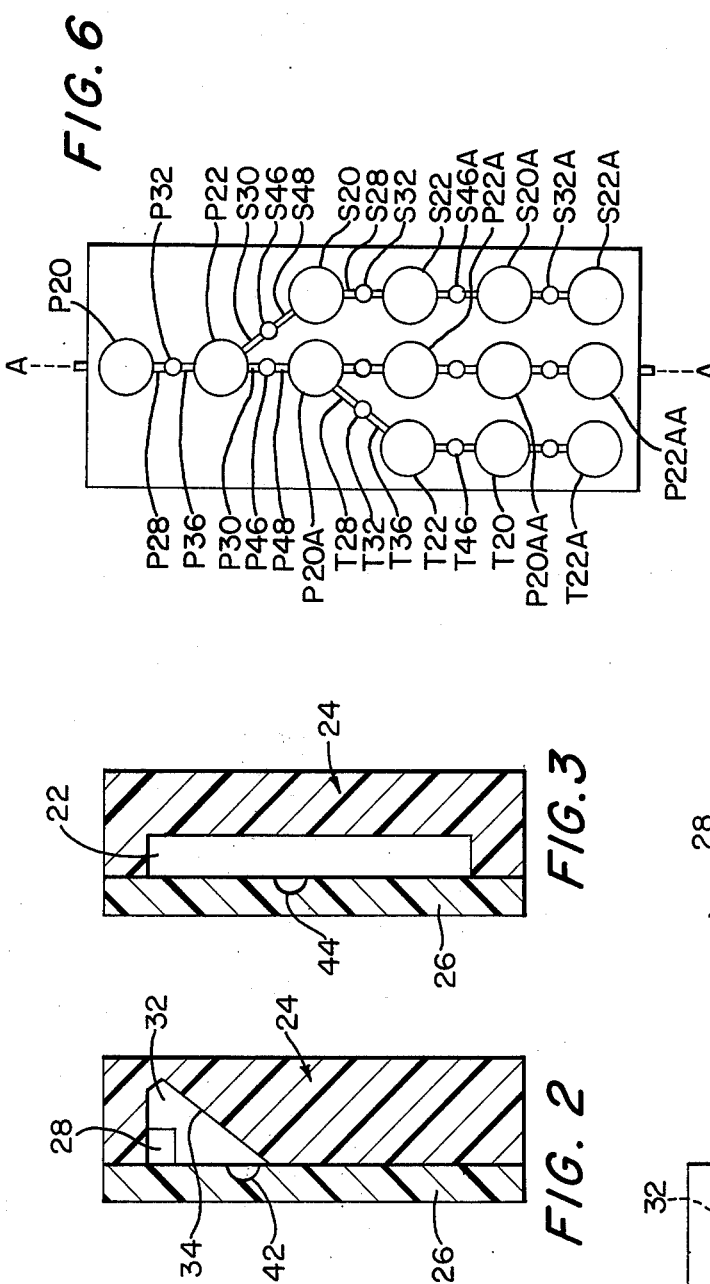
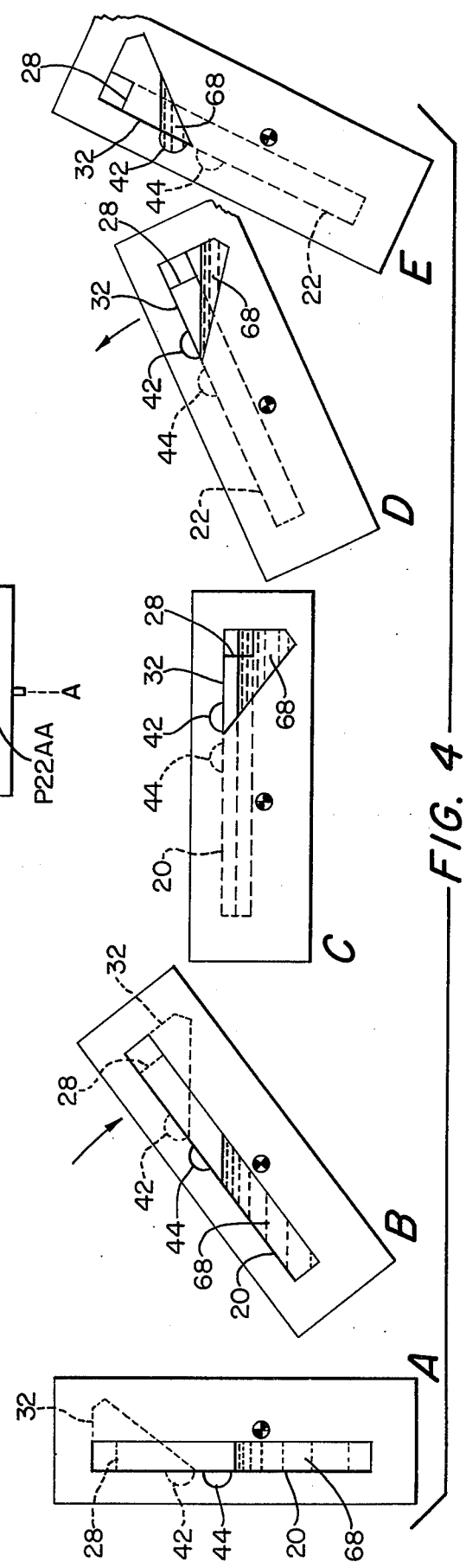

PROPORTIONAL DILUTER

This invention relates to a device for proportional dilution of liquids.

A very common requirement, both for laboratory purposes and industrial processes, is the preparation of a large number of stock or standard solutions which differ only in the relative proportions of solute and solvent. Typically, one first prepares a strong solution in which the components have been very carefully weighed so that the relative proportions are precisely determined. For example, a 1 M solution of sodium chloride is prepared by weighing out exactly 58.5 grams of salt which are then dissolved in precisely 1000 milliliters of water. This strong solution is then accurately standardized and the weaker strength solutions are prepared from it by quantitative dilution. Thus, 0.1 and 0.01 M solutions of the salt are prepared by diluting aliquots of the 1 M solution with water in proportion of 1:10 and 1:100.

In many instances, a very large number of solutions of the same composition but of different strengths or proportions of materials are desired. For example, in the testing of the efficacy (i.e. minimum lethal dosage) of antibacterial agents, many different concentrations of an agent are employed against a culture. Similarly, a titration generally involves the computation of a function through a series of successive additions of discrete quantities of titrant. The preparation of such large number of solutions of precisely related proportions hitherto has tended to be extremely time-consuming or burdensome, particularly where more than one series of values each covering a large range is involved. A principal object of the present invention is to provide a simple and effective apparatus for providing, with ease, accuracy and speed, a multiplicity of various dilutions of a solution over a wide range. The term "solution" as used herein is intended to include mixtures of miscible liquids as well as liquids with solids soluble therein and particulates, such as microcapsules, which exhibit fluid or quasi-fluid flow characteristics. Mathematically, the processes of providing proportional changes in a liquid in the present invention can be described as recursive procedures, i.e. determination of successive values of a function in which each such value is derived from the value of the immediately preceding value. For example, the successive values $$a_1, \frac{a_1 + b_1}{a_2}, \frac{\frac{a_1 + b_1}{a_2} + b_2}{a_3}$$

are typical recursive values of a function.

Hence, the present invention in a sense provides a fluidic computer for performing a fixed (i.e. "hard-wired") recursive operation in a liquid flow ratioing domain.

Other objects of the present invention will in part be obvious and will in part appear hereinafter.

The invention accordingly comprises the apparatus possessing the construction, combination of elements and arrangement of parts which are exemplified in the following detailed disclosure, and the scope of the application of which will be indicated in the claims.

For a full understanding of the nature and objects of the present invention, reference should be had to the following detailed description taken in connection with the accompanying drawing wherein:

FIG. 2 is a cross-section taken along the line 2—2 of FIG. 1;

FIG. 3 is a cross-section taken along the line 3—3 of FIG. 1.

FIG. 4 is a series of views of the device of FIG. 1, in which the cross-sections of FIG. 2 and 3 are combined, illustrating the operation of the device;

FIG. 6 is a simplified schematic of a branched embodiment of the present invention.

Generally, the device of the present invention comprises a plurality of various chambers sequentially connected to one another. At a minimum, the device includes at least two storage chambers one of which is intended initially to store a supply of liquid to be diluted, the other of which is intended initially to store a supply of the diluent. The device also includes a sampling chamber which is intended to transfer a precisely measured amount of sample of liquid from a first of the storage chambers to the second storage chamber upon each cycle of operation. In one form of the invention, the three chambers are spatially fixed with respect to one another and with respect to an axis of rotation of the device. The entire device is movable, preferably in oscillation, about the axis of rotation. Because of the positioning of the chambers with respect to one another and to the axis of rotation of the device, at the beginning of a cycle of oscillation, liquid in the storage chambers normally remains in the chambers and will not flow out of the latter. After rotation on the device from its initial position through some predetermined angle, liquid in the first storage chamber will flow into the sampling chamber, filling the latter in a predetermined amount. After the sample chamber is filled the device is rotated in the opposite direction. However, because of the relative position of the chambers, liquid in the sampling chamber cannot flow back into the first storage chamber but is "trapped". A conduit is provided so that as the device rotates back toward its initial position, all "trapped" liquid in the sample chamber will flow through the conduit and into the second storage chamber.

Therefore, if the first of the storage chambers in the array of such chambers is initially filled with a first liquid, and all of the other storage chambers are initially filled with a diluent, after a number of cycles of oscillation, there will be created a series of successively diluted solutions of the first liquid with the diluent, each in one of the several storage chambers. The relative dilution of the first liquid from storage chamber to storage chamber is a function of a number of parameters, including the relative proportion or sample taken during each cycle from each storage chamber by each sampling chamber, the number of storage and associated sampling chambers in the device, and the number of cycles through which the device is operated.

Figure 1:
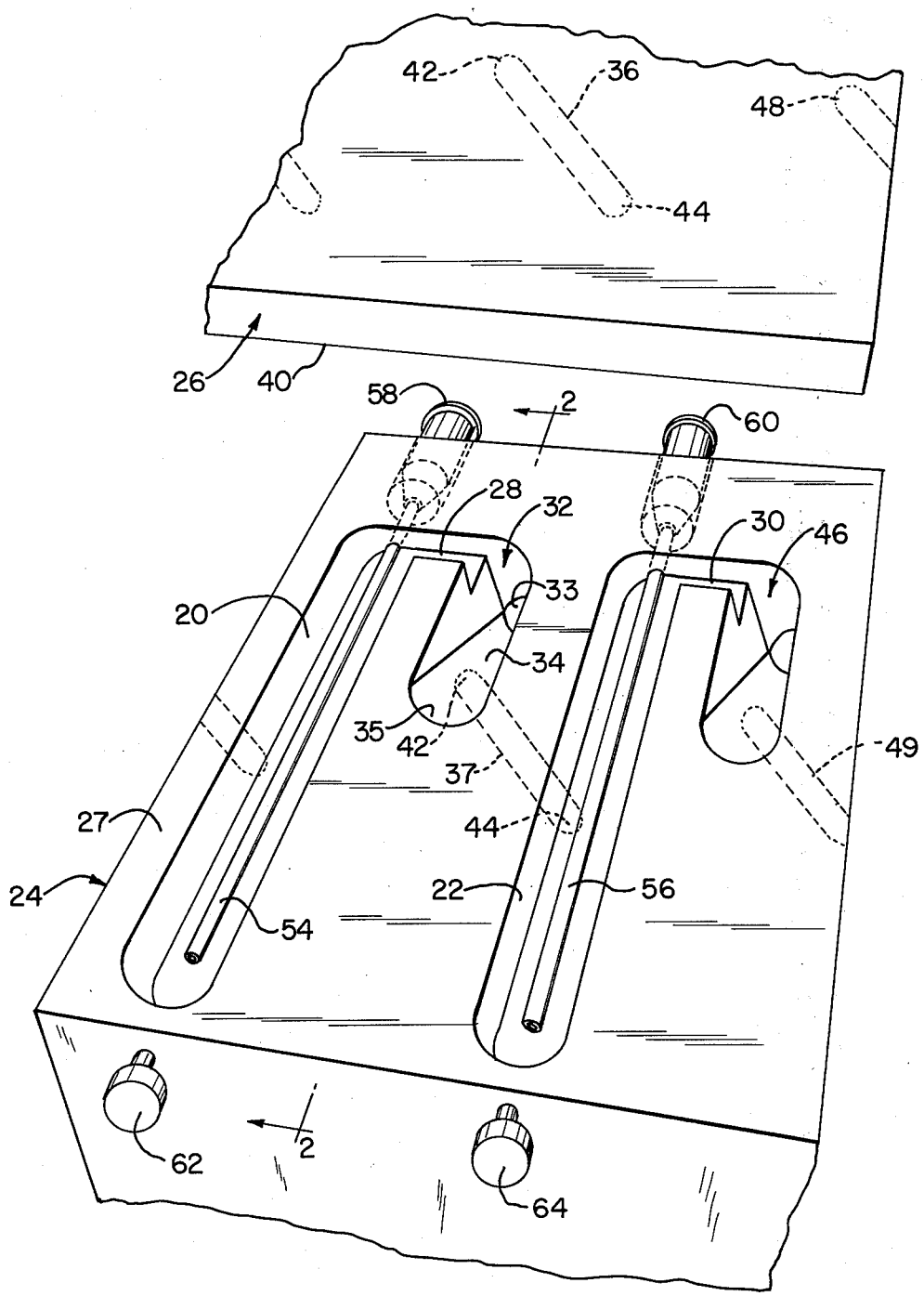
FIG. 1 is an isometric exploded view, partly in phantom, of a device embodying the principle of the present invention.

Referring now to the drawing, there will be seen in FIG. 1 an isometric projection of an exemplary embodiment of the invention. For ease in illustration, the embodiment of FIG. 1 is shown as if it were made of a transparent material such as glass, a synthetic polymer or the like, and can in practice be made of these materials or of a large variety of other materials as will be apparent hereinafter. The device includes at least two storage chambers 20 and 22 shown formed as a pair of elongated recesses or slots molded or milled into a base block 24 of material which is substantially chemically inert to any liquid to be used with the device. Chambers 20 and 22 are also bounded by cover plate 26, shown for convenience exploded away from block 24, but which is normally preferably sealed to surface 27 of block 24, as by bolts, adhesives or other sealing means. The axes of elongation of storage chambers 20 and 22 preferably lie parallel with one another so that the storage chambers are in a serial array (particularly when there are more than two such chambers) in a common plane defined for example by surface 27. Storage chamber 20 is provided adjacent one end thereof with an open exit channel or port 28, and storage chamber is likewise provided with a similar port 30. The ports are dimensioned so that their cross-section extends substantially across the communicating cross-section of the respective storage chamber.

Connected to exit port 28 is sampling chamber 32 which is provided, adjacent exit port 28, with a deep section 33 extending well below the opening of port 28 into the sampling chamber. The latter is also provided with floor 34 extending from deep section 33 on an incline to meet surface 27 of block 34 at lip 35. Sampling chamber 32 is preferably positioned between storage chamber 20 and 22. The volume of storage chamber 32 is preferably a predetermined proportion of and is smaller than the volume of chamber 20. Thus, samples taken from chamber 20 by sampling chamber 32 are always a fixed volume which is only a part of the total liquid initially stored in chamber 20.

The device also includes conduit means, in the form of an open channel 36 which is cut, molded or milled into surface 40 of cover plate 26 (surface 40 being intended to contact surface 27 in a sealing relation when the device is fully assembled). Conduit 36 is positioned and dimensioned (as shown by the projection of the conduit onto surface 27 by broken line denoted at 37) so that when plate 26 is properly registered in sealing relation with surface 27, one end of conduit 36 communicates with sampling chamber 32 adjacent lip 35, and the opposite end of conduit 36 communicates with and forms open inlet port 44 for chamber 22 intermediate the ends of the latter.

In similar manner, the device of FIG. 1 includes another sampling chamber 46 and another conduit 48 (the projection of which onto surface 27 is shown at 49) which serves to couple the shallow end of the floor of sampling chamber 46 to form an open outlet port for the latter. Means in the form of tubes 54 and 56 are disposed coaxially with respect to storage chambers 20 and 22 respectively for filling the storage chambers with particular liquids. Tubes 54 and 56 are coupled to corresponding external fittings 58 and 60 which can be used to connect tubes 54 and 56 to flexible supply lines, valves or the like (not shown). The ends of storage chambers 20 and 22 opposite fittings 58 and 60 are respectively provided with removable drain plugs 62 and 64.

In use, the device of FIG. 1 is oriented so that the axes of elongation of the storage chambers are substantially vertical with respect to gravity, and sampling chamber 32 and conduit 28 are located adjacent the upper end of storage chamber 20. FIG. 2 is a schematic cross-section taken through sampling chamber 32 of a fully assembled form of the device of FIG. 1, and FIG. 3 is a similar cross-section taken through a storage chamber of the device, both showing the preferred initial vertical orientation of the device.

In operation, the device of FIG. 1 is oscillated, either mechanically or simply by hand, about an axis indicated by the line A—A, between the initial vertical position of the device as shown in FIGS. 2 and 3 and an extreme position wherein the axes of elongation of the storage chambers are horizontal and each sample chamber lies below the respective storage chamber with which it is connected through a port such as 28. Axis A—A is preferably perpendicular to the axes of elongation of the storage chambers and is parallel to the common plane (typified by surface 27) which intersects all of the storage chambers.

The storage chambers are initialy filled with liquid, typically in an amount considerably greater than the total amount of liquid which can be taken from the storage chamber to fill the connecting sample chamber. One can assume that storage chamber 20 is first filled through tube 54, when the chamber is in its vertical position, with a desired amount of a first liquid which may be either the liquid to be diluted or the diluent (or the solvent or solute, as the case may be). In like manner, chamber 22 is similarly filled through tube 56 (in vertical position) with the other of the two liquids being used. The device is then oscillated or rocked back-and-forth about axis A—A between its initial vertical position and its extreme position. The transfer of liquid effected by the oscillation can then be most readily described in connection with the series of views shown in FIG. 4 which illustrate schematically a number of cross-sections (similar to FIGS. 2 and 3) showing the relation between the storage chambers, sampling chamber and ports of the device of FIG. 1 and the liquid therein as the angular orientation of the device changes with oscillation. The axis A—A, being vertical to the plane of the drawing in FIG. 4, is shown by a crossmark or x in each of the several views. Thus, FIG. 4A shows the device in a vertical position, with storage chamber 20 filled with liquid 68, both chamber 20 and its inlet port being outlined in solid line and the adjoining sample chamber 32, port 28 and end 42 of conduit 36 being shown in dotted lines. FIG. 4B shows the same cross-section schematic of FIG. 4A but now turned through a portion of the total angle between the initial vertical position and the extreme horizontal position. FIG. 4C shows the device as it reaches the extreme horizontal position, sample chamber 32, port 28 and end 42 of conduit 36 all now being outlined in solid line with the dotted line indicating chamber 20. In FIG. 4C liquid 68 now occupies space in storage chamber 20, port 28 and sample chamber 32, maintaining a common level in both the storage and sampling chambers by virtue of the fluid passage provided by the orientation of port 28 and the relative position of the two chambers. Having reached the extreme position of FIG. 4C, the device is then rotated in the opposite direction back toward the vertical position. As this latter motion takes place, the level of the liquid in sample chamber 32 tilts and liquid in the sample chamber is unable to now flow back through open port 28 by gravity to chamber 20. This change in level is illustrated in FIG. 4D wherein sample chamber 32, port 28 and end 42 are all outlined in solid line but the dotted line now illustrates the position of chamber 22 and end 44 of conduit 36. As the device rotates further back toward its original vertical position, the liquid in chamber 32 then spills out of the latter into conduit 36 and thence into chamber 22, all as shown in FIG. 4E in which chamber 32 and end 42 of conduit 36 are outlined in solid lines and chamber 22 and end 44 of conduit 36 are shown in dotted lines. Of course, one assumes that chamber 22 has sufficient empty volume to accomodate the liquid transferred by chamber 32.

It will be apparent that in operation of the device of FIG. 1, during oscillations, liquid is transferred from chamber to chamber through simple open ducts and only by the force of gravity, no pump pressures, valves or the like being required. Because of the particular fixed orientation or spatial relation maintained by the various chambers and ducts while in oscillation, during each cycle there is transferred from each storage chamber to the next storage chamber in serial order, a fixed amount of liquid. Assuming that the first storage chamber or stage of the device holds a sample liquid to be diluted and all the other successive storage chambers (each identical to the first storage chamber) thereafter initially hold a diluent, the operation of the system can then be described by the following equation, assuming identical sampling chambers so that the entire system is iterative:

$$C_{a,b} = \frac{1}{n} D_{a-1,b-1} + \left[1 - \frac{1}{n}\right] C_{a,b-1} \tag{1}$$

where $a$ is the number of the stage in the series of stages, $b$ is the number of cycles in a series of cycles, C is the concentration, and $n$ is the total number of stages in the series of stages.

The application of the above equation can be advantageously described in connection with the device shown in FIG. 5 which essentially illustrates a ten-stage dilution system employing the principles of the device of FIG. 1. It will be seen that the various parts of the device of FIG. 5 are shown only schematically and that successive pairs of storage chambers and their associated sampling chambers are numbered in accordance with the identification numeration of FIG. 1.

Figure 5:
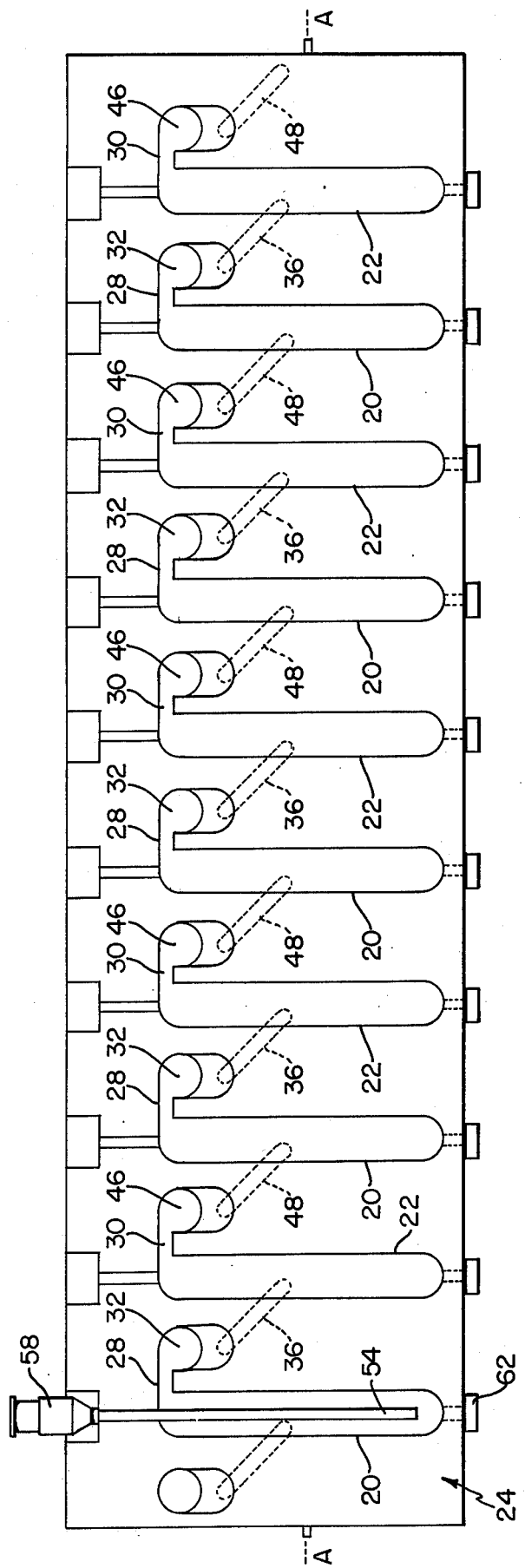
FIG. 5 is a schematic view of yet another embodiment of the invention.

In operation of the device of FIG. 5 the entire array of chambers is oscillated as a unit between an upright position as previously described, and a horizontal position through a series of cycles. If the leftmost chamber 20 (which is the only one shown with a fitting 58 and tube 54 for the sake of ease in illustration) is kept filled through tube 54 with a first solution or liquid to be diluted and all other chambers 20 and 22 are initially filled with a diluent, then for the first $n-1$ cycles of operation, only pure diluent will issue from conduit 48 connected to the output of the last (or furthest to the right in the drawing) chamber 22. For the next $(n-1)^2$ cycles of operation sample liquid will issue from that conduit 48 over a range of dilutions and finally at a constant dilution for $n$ more cycles. At the end of a predetermined number of cycles, of course, the sample will exist in the several chambers 20 and 22 over a large range of dilutions and can then be drawn off as through plug 62 or 64, as the case may be, of one or more particular storage chambers, instead of ultimately from the last conduit 48.

The embodiment of FIG. 5 can be made so that each storage chamber has substantially the same structure and volume as the other storage chambers, and each sampling chamber has substantially the same structure and volume as the other sampling chamber. In such case, the equation heretofore adduced will be seen to be non-linear as noted. However, it will be apparent that the progressive changes in concentration occuring at each stage can be varied considerably. For example, the relationship of each successive storage chamber can differ in volume by some variable, so that the change in volume from stage to stage can be expressed as some arbitrary function. Similarly, the respective volumes of the sampling chambers can vary according to some arbitrary function. In this manner, one can provide a device which is capable of dilution simply and automatically in accordance with a very large number of completely arbitrary functions.

In the system thus described, separation and quantification are accomplished through gravity-impelled flow, but the system need not be so limited. For example, positive pressure feed, as through pneumatic or hydraulic pressure (as from an immiscible fluid) applied to each chamber, can be used to overcome surface tension effects and the like which would otherwise tend to limit the rate at which rocking would provide accurate quantification.

The system of the present invention is also particularly useful for complex operations involving more than a single independent variable. For example, the system can be used to determine the minimum lethal dosage of several different antibiotic or antibacterial agents and mixtures thereof simultaneously with respect to a bacterial culture, or determine multiple end points in a simultaneous titration, and the like. To this end, the system can be branched, i.e. instead of one sample chamber being provided for each storage chamber, one or more of the latter are connected to two or more sampling chambers. Thus, upon each cycle of the operation of the device, parallel samplings can be achieved and transferred to corresponding storage chambers into which respective antibiotic agents can be introduced and then sequentially diluted in a corresponding linked succesion of storage and sampling chambers.

For example, as shown in a simplified schematic diagram in FIG. 6, a device of the present invention is formed in which initial storage chambers P20 is connected through channel P28 to sampling chamber P32, the latter being connected through channel P36 to storage chamber P22. In like manner storage chamber P22 is connected through channel P30 to sampling chamber P46, the latter being connected through channel P48 to storage chamber P20A.

In like manner, chamber P20A is coupled to successive alternate sampling and storage chambers in a series indicated by the letter prefix P. It will be recognized that the chain of chambers and channels thus prefixed with the letter P in FIG. 6 is simply a device substantially identical to that shown in FIG. 5, the coupling being such that rotation of the device of FIG. 6 about axis A—A will cause fluid transfer in the same manner as described in connection with the operation of the device of FIG. 5.

However, as shown in FIG. 6, storage chamber P22 is also connected through a second conduit S30 to sampling chamber S46 which in turn is coupled through conduit S48 to storage chamber S20. Storage chamber S20, as shown, constitutes the first in a series of successive storage and sampling chambers in an array similar to the device of FIG. 5 and prefixed with the letter S.

Also in FIG. 6 storage chamber P20A is connected through a second channel T28 to sampling chamber T32, the latter being connected through channel T36 to storage chamber T22. Storage chamber T22 will be seen to constitute the first in a series of successive storage and sampling chambers prefixed with the letter T, which series is also an array similar to that of FIG. 5.

In an exemplary operation of the device of FIG. 6, typically a solution of an antibiotic is introduced into storage chamber P20, a neutral diluent into storage chambers P22 and P20A and a solution of known concentration of a first bacterial culture into all of the other storage chambers identified by the letter prefix P. A solution of known concentration of a second bacterial culture is introduced into all of the other storage chambers identified by the letter prefix S, and a solution of known concentration of yet a third bacterial culture is introduced into all of the storage chambers indicated by a number prefixed with the letter T. It will be seen that upon operation of the device successive dilutions of antibiotic in the P chain are exposed to the first culture whereby the efficacy of that antibiotic with respect to the bacteria can readily be determined. Simultaneously, the efficacy of the antibiotic with respect to the successive dilutions of the second bacterial culture is achieved in the S chain. The successive dilutions of the antibiotic achieved in the T chain are applied to the third bacterial culture.

Of course, other branched systems can be formed, for example, where the flow proceeds from multiple initial sources to a lesser number or even single fluid storage chamber.

Since certain changes may be made in the above apparatus without departing from the scope of the invention herein involved, it is intended that all matter contained in the above description or shown in the accompanying drawing shall be interpreted in an illustrative and not in a limiting sense.

What is claimed is:

1. A device for proportional liquid dilution, said device comprising in combination:
   a structure including at least two storage chambers and at least one sampling chamber having a fixed volume smaller than either of said storage chambers and communicating between said storage chambers to provide a permanently open path for liquid flow therebetween; and
   means for cyclically operating said device;
   said chambers being so fixedly disposed with respect to one another that during each cycle, liquid in a first of said storage chambers is transferred to fill said sampling chamber and then substantially all liquid in said sampling chamber is transferred to the other of said storage chambers, said transfer between said chambers occurring only in a direction from said first to said other storage chamber.

2. A device as defined in claim 1 wherein said means for cyclically operating said device comprises means for moving said structure between a first position wherein liquid in said first storage chamber will not flow into said sampling chamber and substantially all liquid in said sampling chamber will flow into said other storage chamber; and a second position wherein liquid in said first storage chamber will flow into said sampling chamber but will not flow out of the latter into said second chamber.

3. A device for proportional liquid dilution, said device comprising in combination:
   at least two storage chambers each having an open outlet port and an open inlet port;
   at least one sampling chamber coupled to a first of said storage chambers through the outlet port of the latter, and having a volume which is a predetermined proportion of and smaller than the volume of said first storage chamber; and
   a conduit connecting said sampling chamber with the inlet port of the other of said storage chamber;
   said chambers and said conduit being disposed in fixed spatial relation with one another so as to be oscillatable as a unit between first and second predetermined angular positions, said relation being such that in said first position liquid in said first storage chamber will not flow through the outlet port thereof, and in said second position liquid in said first storage chamber will flow through the outlet port thereof into said sampling chamber but will not flow out of the latter through said conduit, and so that at least at some angular position between said first and second positions liquid in said sampling chamber will flow through said conduit into said other of said storage chambers.

4. A device as defined in claim 3 wherein said spatial relation is such that during oscillation of said unit said flows can be gravity impelled.

5. The device as defined in claim 3 wherein said spatial relation is such that during each cycle of oscillation of said unit from said first to said second position and back to said first position, if the volume of liquid in said first storage chamber is greater than the volume of said sampling chamber, the amount of liquid transferred from said sampling chamber to said other of said storage chambers is a substantially constant volume.

6. The device as defined in claim 3 wherein said storage chambers are aligned along a line substantially parallel to said axis.

7. A device for proportional liquid dilution, said device comprising, in combination:
   a plurality of storage chambers arranged in a first serial array distributed substantially parallel to an axis, each of said storage chambers having an open outlet port and an open inlet port;
   a plurality of sampling chambers in a second serial array each paired with a respective one of said storage chambers by coupling through the outlet ports of the latter, each of said sampling chambers having a volume which is a predetermined proportion of and smaller than the volume of the respective paired storage chamber; and
   a plurality of conduits connecting said each sampling chamber with the inlet port of the next serially adjacent of said storage chambers in said first array;
   said chambers and said conduits being disposed in fixed spatial relation to one another so as to be oscillatable as a unit about said axis between first and second predetermined angular positions, said relation being such that in said first position liquid in said storage chambers will not flow through said outlet ports, and in said second position liquid in said storage chambers will flow through said outlet ports into said paired sampling chambers but will not flow out of the latter and so that at least some angular position between first and second liquid in each of said sampling chambers will flow through respective ones of said conduits into respective ones of said next serially adjacent storage chambers.

8. A device as defined in claim 7 wherein said spatial relation is such that during oscillations of said unit, said flows can be gravity impelled.

9. The device as defined in claim 7 wherein said storage chambers all have substantially identical volumes.

10. The device as defined in claim 7 wherein said sampling chambers all have substantially identical volumes.

11. The device as defined in claim 7 wherein the volumes of said sampling chambers differ from one another serially according to a predetermined mathematical function.

12. The device as defined in claim 7 wherein said storage chambers are elongated with their axes of elongation all parallel to one another and vertically oriented when said unit is in said first position, each of said outlet ports being located adjacent the upper end of a corresponding one of said storage chambers when said unit is in said first position, each of said inlet ports being located at a position intermediate the ends of a corresponding one of said storage chambers.

13. The device as defined in claim 12 including means for injecting liquid directly into each of said storage chambers.

14. Apparatus for performing proportional liquid dilution comprising:

a structure including at least first and second storage chambers and at least a sampling chamber fixedly disposed relative to each other, said sampling chamber communicating with said storage chambers and having a fixed volume smaller than that of either one of said storage chambers;

means for moving said structure between predetermined first and second positions;

said sampling chambers being positioned relative to said storage chambers to permit liquid flow from said first storage chamber to said sampling chamber in said first position only and to permit liquid flow from said sample chamber to said second storage chamber in said second position only.

* * * * *